United States Patent [19]

Kabeta et al.

[11] Patent Number: 4,927,951

[45] Date of Patent: May 22, 1990

[54] ORGANOSILICON COMPOUND

[75] Inventors: Keiji Kabeta; Kiyoaki Syuto, both of Gunma, Japan

[73] Assignee: Toshiba Silicone Co., Ltd., Tokyo, Japan

[21] Appl. No.: 424,394

[22] Filed: Oct. 20, 1989

[30] Foreign Application Priority Data

Nov. 30, 1988 [JP] Japan .................................. 63-303070

[51] Int. Cl.$^5$ .............................................. C07F 7/10
[52] U.S. Cl. ................................................... 556/419
[58] Field of Search ......................................... 556/419

[56] References Cited

U.S. PATENT DOCUMENTS 4,543,398 9/1985 Barry et al. ...................... 556/419 X

FOREIGN PATENT DOCUMENTS 0124017 11/1984 European Pat. Off. ............ 556/419

Primary Examiner—Paul F. Shaver
Attorney, Agent, or Firm—Flynn, Thiel, Boutell & Tanis

[57] ABSTRACT

An organosilicon compound which contains a highly reactive (meth)acrylamide and a siloxane group with a molecule has the following formula:

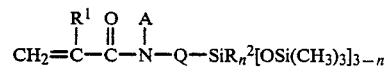

where $R^1$ is a methyl group or hydrogen atom, $R^2$ is a substituted or unsubstituted monovalent hydrocarbon group, Q is a divalent hydrocarbon group having 1–8 carbon atoms, A is a hydrogen atom, substituted or unsubstituted hydrocarbon carbon group or $-QSiR^n_2[OSi(CH_3)_3]_{3-n}$, and n is an integer from 0–2.

6 Claims, No Drawings

ORGANOSILICON COMPOUND

FIELD OF THE INVENTION

This invention relates to a new organosilicon compound and more specifically, relates to a new organosilicon compound which contains a highly reactive (meth-)acrylamide group and a siloxane group within a molecule.

PRIOR ART

Compounds containing siloxane bonds have frequently been used in the past as a component of various types of polymers for reasons such as having good oxygen permeability as well as good heat and weather resistance. From among such compounds, compounds which have portions that possess reactive functional groups and siloxane bonds within the same molecule have come to be known as useful materials that are able to give the various properties of silicon to existing organic resins by utilizing their reactive functional groups.

For example, an organosilicon compound which possesses highly reactive double bonds,

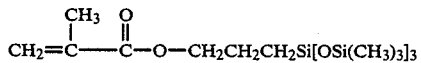

is used for this purpose and is industrially produced. It has been disclosed that this compound can be utilized as a hard contact lens material [U.S. Pat. No. 3 808 178 Specifications (1974)], and as a double-layer resist upper layer having favorable ion etching properties and resistance to reaction with oxygen ($O_2$—RIE resistance) by copolymerizing it with methyl methacrylate [SPIE, Vol. 469, Advances in Resist Tech., (1984)].

Notwithstanding, when using this compound as, for example, a hard contact lens material, there still are areas in which it is unsatisfactory, such as its oxygen permeability, and similarly, when using this compound as a resist material, it is still unsatisfactory in terms of its $O_2$-RIE resistance.

OBJECT OF THE PRESENT INVENTION

The object of the present invention is to provide a new and useful organosilicon compound which can be used as a raw material or modifying material for introducing siloxane segments into various types of polymer materials by it possessing highly reactive double bonds as well as portions having a siloxane bonded within the same molecule.

SUMMARY OF THE INVENTION

As a result of earnest studies to accomplish the object stated above, the present inventors were able to complete and provide this invention by synthesizing an organosilicon compound of the general formula:

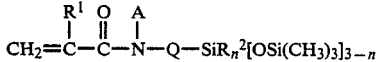

where $R^1$ is a methyl group or hydrogen atom, $R^2$ is a substituted or unsubstituted monovalent hydrocarbon group, Q is a divalent hydrocarbon group having 1-8 carbon atoms, A is a hydrogen atom, or unsubstituted hydrocarbon group or —$QSiR_n^2[OSi(CH_3)_3]_{3-n}$, and n is an integer from 0-2

BRIEF DESCRIPTION OF THE DRAWINGS

FIG. 1 and FIG. 2 are the NMR and IR spectra of the compound of this invention obtained in Example 1.

DETAILED DESCRIPTION

In other words, this invention relates to a new organosilicon compound which possesses highly reactive double bonds and siloxane bonding portions within the same molecule indicated above.

The organosilicon compound of this invention is synthesized, for example, using the reactions indicated below.

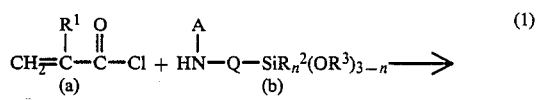

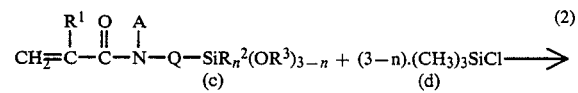

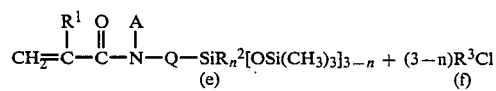

In this case, $R^1$, $R^2$, A, Q and n in the synthesis process are as described previously, and $R^3$ is an alkyl Here, $R^1$ is a hydrogen atom or a methyl group. Examples of the substituted or unsubstituted monovalent hydrocarbon groups represented by $R^2$ include an alkyl group such as a methyl, ethyl, propyl, butyl or hexyl group, a cycloalkyl group such as a cyclopentyl or cyclohexyl group, an aralkyl group such as a 2-phenylethyl group, an aryl group such as a phenyl or tolyl group, and a substituted hydrocarbon group such as a chloromethyl, chlorophenyl or a 3,3,3-trifluoropropyl group.

In addition, although A is a hydrogen atom, or unsubstituted hydrocarbon group or —$QSiR_n^2[OSi(CH_3)_3]_{3-n}$. from the viewpoint of the compound's siloxane content, it is preferable that it be —$QSiR_n^2[OSi(CH_3)_3]_{3-n}$.

In addition, although examples of Q include divalent hydrocarbon groups such as a methylene, ethylene, propylene, butylene or phenylene group, from the viewpoint of ease of acquisition as a raw material, etc., a propylene group is preferable.

In addition, although examples of $OR^3$ include a methoxy, ethoxy, propoxy or butoxy group, from the viewpoint of ease of acquisition and suitable reactivity, a methoxy group or ethoxy group is preferable.

From among these silane compounds specific examples of the compound which corresponds to (b)

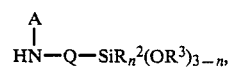

an important raw material of this invention, include N-e 3-aminopropyltrimethoxysilane, N-allyl-aminopropyltrimethoxysilane, N-phenyl-3-allylpropyltrimethoxysilane, N- N-bis[3-(trimethoxysilyl)propyl]amine, and N,N-bis[3-(methyldimethoxysilyl)propyl]amine.

First, the reaction between (meth)acryloyl chloride (a) and an amino group-containing silane compound (b) indicated in (1) will be described. In this reaction, a dehydrochlorination agent is required since hydrogen chloride is produced. Although it is possible to use the amino group-containing silane compound, the reaction raw material, in excess for this purpose, normally, another amine which does not react with (meth)acryloyl chloride is added to the ethylamine, tributylamine and N-methylmorpholine. The amount of this amine that is added must be at least equivalent to the amount which neutralizes the hydrogen chloride which is produced as a by-product. Normally, 1.0–1.5 equivalents are used with respect to the (meth) acryloyl chloride. If more than this amount is used, the reaction is slowed, which causes the reaction mixture to become too basic and results in the disadantage of a decrease in the stability of the product.

The charging ratio of the amino group-containing silane compound (b) to the (meth) acryloyl chloride (a) is roughly 1.0 equivalent, and preferably, 0.95–1.05 equivalents. If it is less than 0.95 equivalent, (meth)acryloyl chloride will remain unreacted in large amounts. In addition, if it is greater than 1.05 equivalents, conversely, the silane compound will remain unreacted in large amounts, making this reaction economically disadvantageous. However, in the case of also using the silane compound as the above mentioned dehydrochlorination agent, it is only natural that the charging ratio, with respect to the (meth)acryloyl chloride, be dependent upon the amount of amine, in the form of the dehydrochlorination agent, that was added. In other words, since 2.0–2.5 equivalents is suitable for the total amount of amine required in the reaction mixture with respect to the (meth) acryloyl chloride, it is preferable to charge an amount of silane compound that is the difference of the amount of amine that was actually added in the form of the dehydrochlorination agent and this amount.

Although this reaction is normally accomplished by adding (meth) acryloyl chloride (a) into a mixed solution of the amino group-containing silane compound (b), the raw material, and the amine used for dehydrochlorination, a solvent may be used in order to facilitate temperature control and stirring. Examples of such a solvent include hydrocarbon-type solvents like toluene, xylene, dichlorohexane, n-hexane, n-heptane, naphtha, mineral spirit and petroleum benzine, halogenated hydrocarbon-type solvents like chloroform, carbon tetrachloride, trichloroethylene, perchloroethylene and 1,1,1-trichloroethane, ether-type solvents like ethyl ether, tetrahydrofuran and ethylene glycol diethyl ether, ester-type solvents like ethyl acetate, butyl acetate and amyl acetate, as well as aprotic solvents like dimethylformamide and dimethylacetoamide.

Since the reaction time varies according to the raw material used, catalyst or solvent, and reaction temperature, etc., it is not subject to any particular limitations. However, the conditions are normally set so that the reaction is completed in 0.5–6 hours.

Following completion of the reaction, after removing the hydrochloride of the amine by filtration or washing, the compound that has been obtained can be purified by methods such as distillation, gas chromatography separation, liquid chromatography separation or column chromatography since the product compound has been obtained as a result of a highly selective reaction.

In order to increase the stability of the raw material and product during the reaction and purification, a commonly known and suitable polymerization inhibitor and antioxidant may be added as a routine measure.

Continuing, the following describes the reaction between the (meth)acrylamide derivative (c) obtained by the reactions described above, and trimethylchlorosilane (d), in other words, the reaction indicated as (2). This reaction is a previously known reaction, and is normally accomplished by adding the above-mentioned (meth)acrylamide derivative (c) and trimethylchlorosilane (d) into a mixed solution of water, methanol and hexane. Following completion of the addition, the target compound (e) of this invention can be obtained by purification by separating the aqueous layer and concentrating the organic layer.

Since the reaction time varies according to the raw material used, catalyst or solvent, and reaction temperature, etc., it is not subject to any particular limitations. However, conditions are normally set so that the reaction is completed in 0.5–6 hours.

The target compound can be purified by using commonly known purification methods similar to those of the previous method. In addition, a polymerization inhibitor and antioxidant may be added during the reaction and the purification conducted in the same manner as the previous method.

As is clear from its structure, since the organosilicon compound of this invention is a compound which contains a (meth)acryl group and a portion having siloxane bonding within the same molecule, it can be used as a raw material for the introduction of siloxane portions into various organic polymers. In addition, it is also effective and useful as a modifier which introduces siloxane segments into existing organic polymers by graft copolymerization.

EXAMPLES

Hereafter the present invention will be described in more detail by referring to the examples but is not deemed to be limited only to these examples. Parts are all by weight, unless otherwise indicated.

EXAMPLE 1

170 parts of N,N-bis(3-trimethoxysilylpropyl)amine, 50 parts of triethylamine, 580 parts of anhydrous benzene, and 0.2 parts of phenothiazine as a polymerization inhibitor were charged to a three-necked flask equipped with a thermometer a reflux condenser to which was attached a calcium chloride tube, and a dropping funnel. 52 parts of methacryloyl chloride dissolved in 110 parts of anhydrous benzene were added dropwise to this mixture over the course of roughly 20 minutes while cooling the mixture in ice. The reaction temperature was from 5°–15° C. Following completion of the addition, the reaction was allowed to proceed for another 2 hours at room temperature. After filtration of the salt that was produced in the preceding reaction, benzene was removed from the reaction mixture by distillation under a reduced pressure.

Then, 153 parts of a colorless, transparent liquid was obtained by gas chromatographic separation from the oily matter that was obtained from the distillation. The yield was 74% of the theoretical amount.

A reaction was then conducted with the N,N-bis(3-trimethoxysilylpropyl)methacrylamide that was obtained. In other words, 370 parts each of water, n-hexane and methanol were placed in a flask equipped with a dropping funnel, reflux condenser and thermometer. A mixture of 153 parts of N,N-bis(3-trimethoxysilylpropyl)methacrylamide, 486 parts of trimethylchlorosilane, and 0.142 parts of 2,6-ditert-butyl-p-cresol, a polymerization inhibitor, was added dropwise over the course of roughly 1 hour while cooling and stirring with a stirrer. Following completion of the addition, the reaction mixture was stirred for roughly 1 hour at room temperature. Following this, the organic layer was separated and was washed with saturated saline solution. After the removal of the water with anhydrous sodium sulfate and separation by filtration, the solvent was removed by distillation under a reduced pressure to obtain the target product. When NMR, IR, mass spectroscopy and elemental analysis were performed on this compound, it was found to be N,N-bis[3-tris(trimethylsiloxy)silylpropyl]methacrylamide. 123 parts of the compound was obtained for a yield of 44%. In addition, the refractive index was 1.4344 $n_d^{25}$. Diagrams of the NMR and IR spectra are shown in FIGS. 1 and 2, and the results of the analyses are summarized in Table 1.

EXAMPLE 2

219 parts of 3-(N-allyl)aminopropyltrimethoxysilane, 101 parts of triethylamine, 1400 parts of anhydrous benzene and 105 parts of methacryloyl chloride were allowed to react in the same manner as in Example 1. As a result, 198 parts of N-allyl-N-(3-trimethoxysilyl)propylmethacrylamide was obtained. The yield was 69%.

Continuing, the methacrylamide derivative obtained here was allowed to react with 450 parts of trimethylchlorosilane in a mixed solution of 200 parts each of water, methanol and hexane. Following this reaction, when the organic layer was separated and the solvent removed, 178 parts of a colorless, transparent liquid was obtained. As a result of performing the same analyses as those of Example 1 on this compound, the compound was found to be N-allyl-N-[3-tris(trimethylsiloxy)silyl-propyl]methacrylamide. The yield was 56%. The results of the analyses are summarized in Table 1.

EXAMPLE 3

239 parts of N-phenyl-3-aminopropylmethyldimethoxysilane, 101 parts of triethylamine, 1400 parts of anhydrous benzene and 105 parts of methacryloyl chloride were allowed to react in the same manner as in Example 1. 224 parts of N-phenyl-N-(3-methyldimethoxysilyl)propylmethacrylamide was obtained. The yield was 73%.

Then, this compound was allowed to react with 317 parts of trimethylchlorosilane in a mixed solution of 250 parts each of water, methanol and hexane. Following this reaction, when the organic layer was separated and the solvent was removed, 201 parts of a colorless, transparent liquid were obtained. As a result of performing the same analyses as those of Example 1 on this compound, it was found to be N-phenyl-N-[3-methylbis(trimethylsiloxy)silylpropyl]methacrylamide. The yield was 65%. The results of the analyses are summarized in Table 1.

TABLE 1

|  | Example 1 | Example 2 | Example 3 |
|---|---|---|---|
|  | [structure: CH₂=C(Me)−C(=O)−N[−(CH₂)₃−Si(OSiMe₃)₃]₂] | [structure: CH₂=C(Me)−C(=O)−N(allyl)−(CH₂)₃−Si(OSiMe₃)₃] | [structure: CH₂=C(Me)−C(=O)−N(Ph)−(CH₂)₃−SiMe(OSiMe₃)₂] |
| NMR (CCl₄ δ) | 0.07(s, 54H, Si—CH₃)<br>0.17–0.55(m, 4H, Si—CH₂—)<br>1.08–1.75(m, 4H, C—CH₂—C)<br>1.85(s, 3H, C—CH₃)<br>3.20(t, J=7Hz, 4H, N—CH₂—)<br>4.87(s, 1H, olefinic)<br>5.00(s, 1H, olefinic) | 0.07(s, 27H, Si—CH₃)<br>0.20–0.55(m, 2H, Si—CH₂)<br>1.32–1.72(m, 2H, C—CH₂—C)<br>1.85(s, 3H, C—CH₃)<br>3.20(t, J=7Hz, 2H, N—CH₂)<br>3.85(d, J=6Hz, 2H, C=C—CH₂—N)<br>4.89–5.27(m, 4H, olefinic)<br>5.55–6.00(m, 1H, olefinic) | 0.07(s, 21H, Si—CH₃)<br>0.20–0.55(m, 2H, Si—CH₂)<br>1.30–1.70(m, 2H, C—CH₂—C)<br>1.85(s, 3H, C—CH₃)<br>3.22(t, J=7Hz, 2H, N—CH₂)<br>4.95(s, 1H, olefinic)<br>5.10(s, 1H, olefinic)<br>6.40–7.35(m, 5H, aromatic) |
| IR (cm⁻¹) | 3080(olefinic CH)<br>2950(CH)<br>1630(C=O, C=C)<br>1250(Si—CH₃)<br>1180(Si—O—Si)<br>1050(Si—O—Si) | 3080(olefinic CH)<br>2950(CH)<br>1640(C=O, C=C)<br>1250(Si—CH₃)<br>1180(Si—O—Si)<br>1050(Si—O—Si) | 3080(olefinic CH)<br>3050(aromatic CH)<br>2950(CH)<br>1630(C=O)<br>1500(aromatic C—C)<br>1250(Si—CH₃)<br>1180(Si—O—Si)<br>1050(Si—O—Si) |
| Mass (M⁺) | 757 | 461 | 423 |
| Elemental Analysis (calculated values) | C 55.05(44.34)<br>H 9.64(9.43)<br>N 1.90(1.85)<br>Si 29.50(29.62) | C 49.20(49.41)<br>H 9.43(9.38)<br>N 3.21(3.03)<br>Si 44.27(24.32) | C 56.48(56.69)<br>H 8.91(8.80)<br>N 3.42(3.30)<br>Si 19.74(19.88) |

What is claimed is:

1. An organosilicon compound of the general formula:

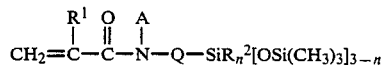

$$CH_2=C-\underset{\underset{O}{\|}}{C}-\underset{\underset{R^1}{|}}{N}-Q-SiR_n^2[OSi(CH_3)_3]_{3-n}$$
(with A on nitrogen)

where R¹ is a methyl group or hydrogen atom, R² is a substituted or unsubstituted monovalent hydrocargon group, Q is a divalent hydrocarbon group having 1–8 carbon atoms, A is a hydrogen atom, substituted or unsubstituted hydrocarbon group or —QSiR$_n^2$[OSi(CH₃)₃]$_{3-n}$, and n is an integer from 0–2.

2. An organosilicon compound as described in claim 1 in whihc R¹ is an ethyl group.

3. An organosilicon compound as described in claim 1 in which A is —QSiR$_n^2$[OSi(CH₃)₃$_{3-n}$ 4. An organosilicon compound as described in claim 1, wherein said compound is N,N-bis[3-tris(trimethylsiloxy)-silylpropyl]methacrylamide.

5. An organosilicon compound as described in claim 1, wherein said compound is N-allyl-N-[3-tris(trimethylsiloxy)silylpropyl]methacrylamide.

6. An organosilicon compound as described in claim 1, wherein said compound is N-phenyl-N-[3-methylbis(trimethylsiloxy)silylpropyl]methacrylamide.

* * * * *

UNITED STATES PATENT AND TRADEMARK OFFICE
CERTIFICATE OF CORRECTION

PATENT NO. : 4 927 951
DATED : May 22, 1990
INVENTOR(S) : Keiji KABETA et al

It is certified that error appears in the above-identified patent and that said Letters Patent is hereby corrected as shown below:

Column 6, line 64; change the portion of the formula on this line to read as follows:

$$--- {}^2[OSi(CH_3)_3]_{3-n} ---.$$

Column 6, line 68; change the formula to read as follows:

$$--- -QSiR_n^2[OSi(CH_3)_3]_{3-n} ---.$$

Signed and Sealed this

Eighth Day of October, 1991

Attest:

HARRY F. MANBECK, JR.

Attesting Officer

Commissioner of Patents and Trademarks